United States Patent
Tornier et al.

(10) Patent No.: US 7,462,197 B2
(45) Date of Patent: Dec. 9, 2008

(54) GLENOIDAL COMPONENT OF A SHOULDER PROSTHESIS, SET OF ELEMENTS CONSTITUTING SUCH A COMPONENT AND TOTAL SHOULDER PROSTHESIS INCORPORATING SUCH A COMPONENT

(75) Inventors: Alain Tornier, Saint Ismier (FR); Francois Sirveaux, Villers les Nancy (FR); Gilles Walch, Lyons (FR); Daniel Mole, Nancy (FR); Christophe Levigne, Caluire (FR); Pascal Boileau, Nice (FR); Luc Favard, Montlouis (FR)

(73) Assignee: Tornier SAS, Saint Ismier (FR)

( * ) Notice: Subject to any disclaimer, the term of this patent is extended or adjusted under 35 U.S.C. 154(b) by 294 days.

(21) Appl. No.: 11/151,404

(22) Filed: Jun. 14, 2005

(65) Prior Publication Data
US 2005/0278032 A1 Dec. 15, 2005

Related U.S. Application Data

(60) Provisional application No. 60/579,258, filed on Jun. 15, 2004.

(30) Foreign Application Priority Data
Jun. 15, 2004 (FR) .................................. 04 06473

(51) Int. Cl.
*A61F 2/40* (2006.01)
(52) U.S. Cl. ............... 623/19.13; 623/19.11; 623/19.12
(58) Field of Classification Search .............. 623/18.11, 623/19.11–19.14, 23.4, 23.42
See application file for complete search history.

(56) References Cited

U.S. PATENT DOCUMENTS

| 3,694,820 A | 10/1972 | Scales et al. |
| 3,815,157 A | 6/1974 | Skorecki et al. |
| 3,842,442 A | 10/1974 | Koibel |

(Continued)

FOREIGN PATENT DOCUMENTS

CH 507704 5/1971

(Continued)

OTHER PUBLICATIONS

John M. Fenlin Jr., M.D., Symposium on Surgery of the Shoulder, "Total Glenohumeral Joint Replacement," *Othopedic Clinics of North America*, vol. 6, No. 2, Apr. 1975, pp. 565-583.

(Continued)

*Primary Examiner*—Bruce E Snow
*Assistant Examiner*—Megan Wolf
(74) *Attorney, Agent, or Firm*—Faegre & Benson LLP

(57) ABSTRACT

The glenoidal component for shoulder prosthesis according to the invention comprises a base adapted to be immobilized on a patient's glenoid cavity and an element adapted to be added on the base and defining a convex surface of articulation of which at least a part is globally in the form of a portion of sphere and centred on a geometric point, the base being provided with a part centred on an axis and on which is added the afore-mentioned element. When the component is in assembled configuration, the geometric centre and the afore-mentioned axis are offset with respect to each other.

18 Claims, 3 Drawing Sheets

U.S. PATENT DOCUMENTS

| | | | |
|---|---|---|---|
| 3,864,758 A | 2/1975 | Yakich | |
| 3,869,730 A | 3/1975 | Skobel | |
| 3,916,461 A | 11/1975 | Buechel et al. | |
| 3,978,528 A | 9/1976 | Crep | |
| 3,979,778 A | 9/1976 | Stroot | |
| 3,992,726 A | 11/1976 | Freeman et al. | |
| 4,003,095 A | 1/1977 | Gristina | |
| 4,030,143 A | 6/1977 | Elloy et al. | |
| 4,040,131 A | 8/1977 | Gristina | |
| 4,054,955 A | 10/1977 | Seppo | |
| 4,135,517 A | 1/1979 | Reale | |
| 4,179,758 A | 12/1979 | Gristina | |
| 4,206,517 A | 6/1980 | Pappas et al. | |
| 4,261,062 A | 4/1981 | Amstutz et al. | |
| 4,550,450 A | 11/1985 | Kinnett | |
| 4,693,723 A | 9/1987 | Gabard | |
| 4,822,370 A | 4/1989 | Schelhas | |
| 4,846,840 A | 7/1989 | Leclercq et al. | |
| 4,865,605 A | 9/1989 | Dines et al. | |
| 4,865,609 A | 9/1989 | Roche | |
| 4,892,549 A | 1/1990 | Figgie, III et al. | |
| 4,919,670 A | 4/1990 | Dale et al. | |
| 4,957,510 A | 9/1990 | Cremascoli | |
| 4,963,155 A | 10/1990 | Lazzeri et al. | |
| 5,032,132 A | 7/1991 | Matsen, III et al. | |
| 5,080,673 A | 1/1992 | Burkhead et al. | |
| 5,080,685 A | 1/1992 | Bolesky et al. | |
| 5,127,920 A | 7/1992 | MacArthur | |
| 5,135,529 A | 8/1992 | Paxson et al. | |
| 5,163,961 A | 11/1992 | Harwin | |
| 5,171,289 A | 12/1992 | Tornier | |
| 5,181,928 A | 1/1993 | Bolesky et al. | |
| 5,192,329 A | 3/1993 | Christie et al. | |
| 5,201,882 A | 4/1993 | Paxson | |
| 5,206,925 A | 4/1993 | Nakazawa et al. | |
| 5,222,984 A | 6/1993 | Forte | |
| 5,261,914 A | 11/1993 | Warren | |
| 5,314,479 A | 5/1994 | Rockwood, Jr. et al. | |
| 5,314,485 A | 5/1994 | Judet | |
| 5,314,487 A | 5/1994 | Schryver et al. | |
| 5,326,359 A | 7/1994 | Oudard | |
| 5,330,531 A | 7/1994 | Cappana | |
| 5,358,526 A | 10/1994 | Tornier | |
| 5,383,936 A | 1/1995 | Kubein-Meesenburg et al. | |
| 5,405,399 A | 4/1995 | Tornier | |
| 5,425,779 A | 6/1995 | Schlosser | |
| 5,429,639 A | 7/1995 | Judet | |
| 5,443,519 A | 8/1995 | Averill et al. | |
| 5,458,650 A | 10/1995 | Carret et al. | |
| 5,462,563 A | 10/1995 | Shearer et al. | |
| 5,505,731 A | 4/1996 | Tornier | |
| 5,507,817 A | 4/1996 | Craig et al. | |
| 5,507,818 A | 4/1996 | McLaughlin | |
| 5,507,824 A | 4/1996 | Lennox | |
| 5,549,682 A * | 8/1996 | Roy | 623/19.14 |
| 5,580,352 A | 12/1996 | Sekel | |
| 5,591,168 A | 1/1997 | Judet et al. | |
| 5,662,651 A | 9/1997 | Tornier et al. | |
| 5,676,702 A | 10/1997 | Ratron | |
| 5,702,447 A | 12/1997 | Walch et al. | |
| 5,702,457 A | 12/1997 | Walch et al. | |
| 5,702,478 A | 12/1997 | Tornier | |
| 5,702,486 A | 12/1997 | Craig et al. | |
| 5,723,018 A | 3/1998 | Cyprien et al. | |
| 5,728,161 A | 3/1998 | Camino et al. | |
| 5,741,335 A | 4/1998 | Gerber et al. | |
| 5,755,807 A | 5/1998 | Anstaett et al. | |
| 5,766,256 A | 6/1998 | Oudard et al. | |
| 5,800,551 A | 9/1998 | Williamson et al. | |
| 5,824,106 A | 10/1998 | Fournol | |
| 5,879,395 A | 3/1999 | Tornier et al. | |
| 5,879,405 A | 3/1999 | Ries et al. | |
| 5,902,340 A | 5/1999 | White et al. | |
| 5,910,171 A | 6/1999 | Kummer et al. | |
| 5,928,285 A | 7/1999 | Bigliani | |
| 5,944,758 A | 8/1999 | Mansat et al. | |
| 5,961,555 A | 10/1999 | Huebner | |
| 5,984,927 A | 11/1999 | Wenstrom, Jr. et al. | |
| 6,015,437 A | 1/2000 | Stossel | |
| 6,033,439 A | 3/2000 | Camino et al. | |
| 6,045,582 A | 4/2000 | Prybyla | |
| 6,045,583 A | 4/2000 | Gross et al. | |
| 6,102,953 A | 8/2000 | Huebner | |
| 6,129,764 A | 10/2000 | Servidio | |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,197,062 B1 | 3/2001 | Fenlin | |
| 6,197,063 B1 | 3/2001 | Dews | |
| 6,203,575 B1 | 3/2001 | Farey | |
| 6,206,925 B1 | 3/2001 | Tornier | |
| 6,228,120 B1 | 5/2001 | Leonard et al. | |
| 6,267,767 B1 | 7/2001 | Stroble et al. | |
| 6,283,999 B1 | 9/2001 | Rockwood, Jr. | |
| 6,299,646 B1 | 10/2001 | Chambat et al. | |
| 6,312,467 B1 | 11/2001 | McGee | |
| 6,328,758 B1 | 12/2001 | Tornier et al. | |
| 6,334,874 B1 | 1/2002 | Tornier et al. | |
| 6,364,910 B1 | 4/2002 | Shultz et al. | |
| 6,368,352 B1 | 4/2002 | Camino et al. | |
| 6,368,353 B1 | 4/2002 | Arcand | |
| 6,379,387 B1 | 4/2002 | Tornier | |
| 6,398,812 B1 | 6/2002 | Masini | |
| 6,406,495 B1 | 6/2002 | Schoch | |
| 6,406,496 B1 | 6/2002 | Rüter | |
| 6,436,144 B1 | 8/2002 | Ahrens | |
| 6,436,147 B1 | 8/2002 | Zweymuller | |
| 6,454,809 B1 | 9/2002 | Tornier | |
| 6,458,136 B1 | 10/2002 | Allard et al. | |
| 6,475,243 B1 | 11/2002 | Sheldon et al. | |
| 6,488,712 B1 | 12/2002 | Tornier et al. | |
| 6,494,913 B1 | 12/2002 | Huebner | |
| 6,506,214 B1 | 1/2003 | Gross | |
| 6,508,840 B1 | 1/2003 | Rockwood, Jr. et al. | |
| 6,514,287 B2 | 2/2003 | Ondrla et al. | |
| 6,520,994 B2 | 2/2003 | Nogarin | |
| 6,530,957 B1 | 3/2003 | Jack | |
| 6,540,770 B1 | 4/2003 | Tornier et al. | |
| 6,558,425 B2 | 5/2003 | Rockwood | |
| 6,569,202 B2 | 5/2003 | Whiteside | |
| 6,582,469 B1 | 6/2003 | Tornier | |
| 6,589,281 B2 | 7/2003 | Hyde, Jr. | |
| 6,599,295 B1 | 7/2003 | Tornier et al. | |
| 6,620,197 B2 | 9/2003 | Maroney et al. | |
| 6,626,946 B1 | 9/2003 | Walch et al. | |
| 6,673,114 B2 | 1/2004 | Hartdegen et al. | |
| 6,673,115 B2 | 1/2004 | Resch et al. | |
| 6,679,916 B1 | 1/2004 | Frankle et al. | |
| 6,736,851 B2 | 5/2004 | Maroney et al. | |
| 6,746,487 B2 | 6/2004 | Scifert et al. | |
| 6,749,637 B1 | 6/2004 | Bahler | |
| 6,755,866 B2 | 6/2004 | Southworth | |
| 6,761,740 B2 | 7/2004 | Tornier | |
| 6,767,368 B2 | 7/2004 | Tornier | |
| 6,780,190 B2 | 8/2004 | Maroney | |
| 6,783,549 B1 | 8/2004 | Stone et al. | |
| 6,790,234 B1 | 9/2004 | Frankle | |
| 6,802,864 B2 | 10/2004 | Tornier | |
| 6,824,567 B2 | 11/2004 | Tornier et al. | |
| 6,863,690 B2 | 3/2005 | Ball et al. | |
| 6,875,234 B2 | 4/2005 | Lipman et al. | |
| 6,887,277 B2 | 5/2005 | Rauscher et al. | |

| | | | | | | |
|---|---|---|---|---|---|---|
| 6,890,357 | B2 | 5/2005 | Tornier | 2005/0177241 A1 | 8/2005 | Angibaud et al. |
| 6,890,358 | B2 | 5/2005 | Ball et al. | 2005/0197708 A1 | 9/2005 | Stone et al. |
| 6,942,699 | B2 * | 9/2005 | Stone et al. ............... 623/19.14 | 2005/0203536 A1 | 9/2005 | Laffargue et al. |
| 6,953,478 | B2 | 10/2005 | Bouttens et al. | 2005/0209700 A1 | 9/2005 | Rockwood et al. |
| 6,969,406 | B2 | 11/2005 | Tornier | 2005/0216092 A1 | 9/2005 | Marik et al. |
| 7,011,686 | B2 | 3/2006 | Ball et al. | 2005/0251263 A1 | 11/2005 | Forrer et al. |
| 7,033,396 | B2 | 4/2006 | Tornier | 2005/0256584 A1 | 11/2005 | Farrar |
| 7,066,959 | B2 | 6/2006 | Errico | 2005/0267590 A1 | 12/2005 | Lee |
| 7,108,719 | B2 | 9/2006 | Horber | 2005/0276030 A1 | 12/2005 | Tornier et al. |
| 7,166,132 | B2 | 1/2007 | Callaway et al. | 2005/0278030 A1 | 12/2005 | Tornier et al. |
| 7,169,184 | B2 | 1/2007 | Dalla Pria | 2005/0278031 A1 | 12/2005 | Tornier et al. |
| 7,175,663 | B1 * | 2/2007 | Stone ..................... 623/19.13 | 2005/0278033 A1 | 12/2005 | Tornier et al. |
| 7,195,645 | B2 | 3/2007 | Disilvestro et al. | 2005/0288681 A1 | 12/2005 | Klotz et al. |
| 7,238,207 | B2 | 7/2007 | Blatter et al. | 2005/0288791 A1 | 12/2005 | Tornier et al. |
| 7,238,208 | B2 | 7/2007 | Camino et al. | 2006/0004462 A1 | 1/2006 | Gupta |
| 7,297,163 | B2 | 11/2007 | Huebner | 2006/0009852 A1 | 1/2006 | Winslow et al. |
| 7,309,360 | B2 | 12/2007 | Tornier et al. | 2006/0015185 A1 | 1/2006 | Chambat et al. |
| 7,329,284 | B2 | 2/2008 | Maroney et al. | 2006/0020344 A1 | 1/2006 | Schultz et al. |
| 7,338,498 | B2 | 3/2008 | Long et al. | 2006/0030946 A1 | 2/2006 | Ball et al. |
| 7,338,528 | B2 | 3/2008 | Stone et al. | 2006/0173457 A1 | 8/2006 | Tornier |
| 2001/0032021 | A1 | 10/2001 | McKinnon | 2006/0235538 A1 | 10/2006 | Rochetin et al. |
| 2001/0047210 | A1 | 11/2001 | Wolf | 2006/0241775 A1 | 10/2006 | Buss |
| 2001/0049561 | A1 | 12/2001 | Dews et al. | 2007/0225817 A1 | 9/2007 | Reubelt et al. |
| 2002/0032484 | A1 | 3/2002 | Hyde, Jr. | 2007/0225818 A1 | 9/2007 | Reubelt et al. |
| 2002/0095215 | A1 * | 7/2002 | Camino et al. ........... 623/19.14 | 2007/0225821 A1 | 9/2007 | Reubelt et al. |
| 2002/0099381 | A1 | 7/2002 | Maroney | 2007/0244564 A1 | 10/2007 | Ferrand et al. |
| 2002/0136148 | A1 | 9/2002 | Hyde, Jr. | 2007/0250174 A1 | 10/2007 | Tornier et al. |
| 2002/0143402 | A1 | 10/2002 | Steinberg | | | |
| 2002/0151982 | A1 | 10/2002 | Masini | | FOREIGN PATENT DOCUMENTS | |
| 2003/0009170 | A1 | 1/2003 | Tornier | DE | 19509037 | 9/1996 |
| 2003/0009171 | A1 | 1/2003 | Tornier | DE | 19630298 | 1/1998 |
| 2003/0028198 | A1 | 2/2003 | Tornier et al. | EP | 0257359 | 3/1988 |
| 2003/0074072 | A1 | 4/2003 | Errico et al. | EP | 0299889 | 1/1989 |
| 2003/0097183 | A1 | 5/2003 | Rauscher et al. | EP | 0524857 | 1/1993 |
| 2003/0114933 | A1 | 6/2003 | Bouttens et al. | EP | 549480 | 6/1993 |
| 2003/0149485 | A1 | 8/2003 | Tornier | EP | 0599429 | 6/1994 |
| 2003/0158605 | A1 | 8/2003 | Tornier | EP | 617934 | 10/1994 |
| 2004/0002765 | A1 | 1/2004 | Maroney et al. | EP | 0712617 | 5/1995 |
| 2004/0006392 | A1 | 1/2004 | Grusin et al. | EP | 0664108 | 7/1995 |
| 2004/0030394 | A1 | 2/2004 | Horber | EP | 0679375 | 11/1995 |
| 2004/0034431 | A1 | 2/2004 | Maroney et al. | EP | 715836 | 5/1996 |
| 2004/0039449 | A1 | 2/2004 | Tornier | EP | 0797694 | 10/1997 |
| 2004/0064189 | A1 | 4/2004 | Maroney et al. | EP | 0807426 | 11/1997 |
| 2004/0064190 | A1 | 4/2004 | Ball et al. | EP | 0809986 | 12/1997 |
| 2004/0133276 | A1 | 7/2004 | Lang et al. | EP | 0864306 | 9/1998 |
| 2004/0134821 | A1 | 7/2004 | Tornier | EP | 903128 | 3/1999 |
| 2004/0138754 | A1 | 7/2004 | Lang et al. | EP | 927548 | 7/1999 |
| 2004/0148033 | A1 | 7/2004 | Schroeder | EP | 1062923 | 12/2000 |
| 2004/0193276 | A1 | 9/2004 | Maroney et al. | EP | 1195149 | 4/2002 |
| 2004/0193277 | A1 | 9/2004 | Long et al. | EP | 1380274 | 1/2004 |
| 2004/0193278 | A1 | 9/2004 | Maroney et al. | EP | 1402854 | 3/2004 |
| 2004/0210220 | A1 | 10/2004 | Tornier | FR | 2574283 | 6/1986 |
| 2004/0210317 | A1 | 10/2004 | Maroney et al. | FR | 2652498 | 4/1991 |
| 2004/0215200 | A1 | 10/2004 | Tornier et al. | FR | 2664809 | 1/1992 |
| 2004/0220673 | A1 | 11/2004 | Pria | FR | 2699400 | 6/1994 |
| 2004/0220674 | A1 | 11/2004 | Pria | FR | 2721200 | 12/1995 |
| 2004/0225367 | A1 | 11/2004 | Glien et al. | FR | 2726994 | 5/1996 |
| 2004/0230197 | A1 | 11/2004 | Tornier et al. | FR | 2836039 | 8/2003 |
| 2004/0267370 | A1 | 12/2004 | Ondria | WO | WO 91/07932 | 6/1991 |
| 2005/0008672 | A1 | 1/2005 | Winterbottom et al. | WO | WO 96/17553 | 6/1996 |
| 2005/0015154 | A1 | 1/2005 | Lindsey et al. | WO | WO 98/48172 | 10/1998 |
| 2005/0043805 | A1 | 2/2005 | Chudik | WO | WO 99/49792 | 10/1999 |
| 2005/0049709 | A1 | 3/2005 | Tornier | WO | WO 99/65413 | 12/1999 |
| 2005/0055102 | A1 | 3/2005 | Tornier et al. | WO | WO 00/15154 | 3/2000 |
| 2005/0065612 | A1 | 3/2005 | Winslow | WO | WO 00/41653 | 7/2000 |
| 2005/0085919 | A1 | 4/2005 | Durand-Allen et al. | WO | WO 02/39931 | 5/2002 |
| 2005/0085921 | A1 | 4/2005 | Gupta et al. | WO | WO 02/39933 | 5/2002 |
| 2005/0090902 | A1 | 4/2005 | Masini | WO | WO 03/005933 | 1/2003 |
| 2005/0107882 | A1 | 5/2005 | Stone et al. | WO | WO03/094806 | 11/2003 |
| 2005/0113931 | A1 | 5/2005 | Horber | WO | WO 2007/109319 | 2/2007 |
| 2005/0119531 | A1 | 6/2005 | Sharratt | WO | WO 2007/109291 | 9/2007 |
| 2005/0143829 | A1 | 6/2005 | Ondria et al. | | | |
| 2005/0165490 | A1 | 7/2005 | Tornier | | | |

| WO | WO 2007/109340 | 9/2007 |

OTHER PUBLICATIONS

Boileau et al., U.S. Appl. No. 12/020,913, entitled "Method and Apparatus for Fitting a Shoulder Prosthesis" filed Jan. 28, 2008.
"Aequalis-Fracture Suture Technique in 5 Steps," Tornier, Inc.
"Aequalis-Fracture Shoulder Prosthesis—Surgical Technique," Tornier, Inc.
"Aequalis® Press-Fit Shoulder Prosthesis—Surgical Technique," Tornier, Inc.
"Anatomical Shoulder™ —Cemented Shoulder Prosthesis Product Information and Surgical Technique," Sulzer Medica, 2000.
"Anatomical Shoulder ™ System Surgical Technique—Removable head option for improved surgical results," Zimmer, Inc., 2004.
Bigliani/Flatow® —The Complete Shoulder Solution, 4-Part Fracture of the Humerus Surgical Technique, Zimmer, Inc., 2000.
"Bio-Modular® Bi-Polar Shoulder Arthroplasty," Biomet, Inc., 1997.
"Bio-Modular® Choice, Shoulder System," Biomet Orthopedics, Inc., 2004.
"Bio-Modular Total Shoulder Surgical Technique," Biomet Orthopedics, Inc., 2001.
"Copeland® Humeral Resurfacing Head," Biomet Orthopedics, Inc., 2001.
"Global C.A.P. ® Surgical technique, resurfacing humeral head implant," DePuy International, Ltd., 2004.
Boileau, et al. "Adaptability and modularity of shoulder prosthese," *Maitrise Orthopédique*, https://www.maitriseorthop.com/corpusmaitri/orthopaedic/prothese_epaule_orthop/boileau_us.shtml, Jan. 3, 2006.
Boileau, et al. "Arthroscopic Repair of Full-Thickness Tears of the Supraspinatus: Does the tendon really heal?," *The Journal of Bone and Joint Surgery, Inc.*, pp. 1129-1240, 2005.
"Design Rationale," Latitude®.
Klein, Travis J., et al. "Mechanically favorable bone remodeling rotator cuff arthropathy patients with good function," *Minneapolis Sports Medicine Center and University of Minnesota*.
Mansat, Michel, "Neer 3™ , Surgical Technique for Fractures," Smith & Nephew, 2000.
Molé, M.D., et al., "Aequalis-Reversed® Shoulder Prothesis, Surgical Technique," Tornier, Inc.
Nicholson, Gregory P., "Arthroplasty and Rotator Cuff Deficiency," Chapter 7, pp. 149-166.
"Offset Head, Bio-Modular® Total Shoulder," Biomet, Inc. 2000.
"The Foundation® Total Shoulder Systems," Encore Surgical.
"The Townley Modular Shoulder, Design by Reason," Biopro, Inc.
Zimmer® Bigliani/Flatow® —The Complete Shoulder Solution, Total Shoulder Arthroplasty Surgical Technique, Zimmer, Inc., 2003.
"Zimmer® Shoulder Retractors," Zimmer, Inc., 2000.
"Anatomic Glenoid, Surgical Technique," Smith & Nephew, 2000.
"Anatomical Shoulder® —The new removable head option," Zimmer Inc., 2004.
"Delta CTA® Reverse Shoulder Prosthesis," DePuy International, Ltd., 2004.
Cofield, M.D., Robert H. "Cofield[2] Total Shoulder System, Surgical Technique," Smith & Nephew, 1997.
"Aequalis® -Glenoid Keeled and Pegged—Surgical Techique," Tornier, Inc.
"Bigliani/Flatow® —The Complete Shoulder Solution, Designed by Shoulder Surgeons for Shoulder Surgery," Zimmer, Inc., 2001.
"Tornier Surgical Technique Addendum, Tornier Aequalis® Reversed Hemi-Adaptor Technique," Tornier, Inc., Aug. 8, 2005.
"Tornier Surgical Technique Addendum, Aequalis® Reversed Shoulder Polyethylene Insert," Tornier, Inc., Aug. 8, 2005.
Beuchel M.D., Frederick F. "Beuchel-Pappas™ Modular Salvage Shoulder System," Endotec, Inc., 2000.
Beuchel M.D., Frederick F. "Beuchel-Pappas™ Resurfacing Shoulder System," Endotec, Inc., 2000.
Beuchel M.D., Frederick F. "Beuchel-Pappas™ Total Shoulder System," Endotoec, Inc., 2000.
Hertel M.D., PD, Ralph. "Technical considerations for implantation of EPOCA glenoid components (Leseprobe)," *Epoca Newsletter*, May 14, 2001.
Apoil, André "A Condyle for the Rotator Cuff Muscles, the total shoulder prosthesis," Aesculap® , 1994.
"Tornier Aequalis® Reversed 2 Prong Capsular Retractor," Tornier, Inc., Oct. 8, 2005.
"Tornier Aequalis® Reversed Shoulder G2 Baseplate," Tornier, Inc., Oct. 8, 2005.

* cited by examiner

GLENOIDAL COMPONENT OF A SHOULDER PROSTHESIS, SET OF ELEMENTS CONSTITUTING SUCH A COMPONENT AND TOTAL SHOULDER PROSTHESIS INCORPORATING SUCH A COMPONENT

CROSS-REFERENCE TO RELATED APPLICATIONS

The present application claims priority to prior French Application No. 0406473, filed Jun. 15, 2004, the entire specification of which is hereby incorporated by reference.

FIELD OF THE INVENTION

The present invention relates to a glenoidal component of a shoulder prosthesis as well as to a set of elements constituting such a component, and to a shoulder prosthesis incorporating such a component.

BACKGROUND OF THE INVENTION

In the domain of shoulder prostheses, it is known for example from U.S. Pat. No. 3,978,528, to constitute a so-called "inverted" prosthesis in which a convex articular surface fast with the glenoid cavity and a concave articular surface fast with the humerus, cooperate in order to recreate a joint at the level of the shoulder. In this type of prosthesis, the glenoidal component may be formed, as disclosed for example in FR-A-2 835 425 or WO-A-01/47442, by a base intended to be immobilized on the glenoid cavity and by an element intended to be mounted on this base and defining the convex surface of articulation.

The invention proposes a novel glenoidal component for a shoulder prosthesis which incorporates a base that may present symmetry of revolution, therefore particularly easy to install, but which also makes it possible to adapt the position of the convex articular surface of the glenoidal component to its environment, particularly to the position of the concave humeral articular surface, while facilitating the work of the deltoid muscle in order to limit as much as possible the efforts to be developed by a patient to raise his/her arm fitted with such a prosthesis.

SUMMARY OF THE INVENTION

In that spirit, the invention relates to a glenoidal component of a shoulder prosthesis comprising a base adapted to be immobilized on the glenoid cavity of a patient, as well as an element adapted to be added on this base and defining the convex surface of articulation of which at least a part is globally in the form of a portion of sphere and centred on a geometric point, this base being provided with a part centred on an axis and on which the afore-mentioned element is added. This component is characterized in that, in assembled configuration, the geometric centre of the spherical portion of the surface of articulation and the axis of the afore-mentioned part of the base are offset with respect to each other.

Thanks to the invention, the position of the centre of symmetry of the spherical portion of the convex articular surface is not necessarily aligned with the central axis of the base, this allowing a satisfactory adjustment of the position of the prosthesis with respect to the scapula.

According to advantageous but non-obligatory aspects, a glenoidal component may incorporate one or more of the following characteristics taken in any technically admissible combination:

The afore-mentioned element defines a housing for at least partially receiving the axisymmetric part of the base, this housing being globally centred on another axis which is offset with respect to the afore-mentioned geometric centre, and, when the component is in assembled configuration, substantially merges with the afore-mentioned axis of the base.

When the component is in implanted configuration on the glenoid cavity, the afore-mentioned geometric centre is offset downwardly of the patient's body with respect to the second axis. This makes it possible in particular to avoid interferences between the humeral component of the prosthesis and the pillar of the scapula at the end of the movement of adduction.

The afore-mentioned element is provided with a rear face into which opens out a housing for at least partially receiving the axisymmetric part of the base, while this housing is centred on an axis merged with the axis of the symmetrical part when the component is in assembled configuration.

The element defines a surface for connection between the part of the articular surface globally in the form of a portion of sphere and a portion of the periphery of this rear face.

The afore-mentioned element is selected from a set of elements adapted to be selectively added on the base and of which the geometric centres have different offsets with respect to the axis of the axisymmetric part of the base. Thanks to this aspect of the invention, the offset may be adjusted as a function of the patient's morphology and of the effective position of anchoring of the base on the glenoid cavity.

The part in the form of a portion of sphere is geometrically centred on an axis parallel to the central axis of the afore-mentioned part of the base.

In a variant, the part in the form of a portion of sphere is geometrically centred on an axis which is not perpendicular to a rear face of the component intended to come into abutment against the patient's glenoid cavity. This aspect of the invention makes it possible to control the orientation of the first axis and to position it correctly, including when the milled surface of the glenoid cavity is not parallel to a vertical plane containing the spinal column of the patient standing up, this occurring particularly when the upper part of the scapula is worn or destroyed.

The invention also relates to a set of elements such as the one mentioned above, which are adapted each to be added, in order to constitute a glenoidal element of a shoulder prosthesis, on a base itself adapted to be immobilized on the glenoid cavity of a patient, each element defining a convex surface of articulation of which at least a part is globally in the form of a portion of sphere centred on a geometric point, while each element forms a globally axisymmetric housing for at least partially receiving a part of the base, and the offset between the afore-mentioned geometric centre and the axis of symmetry of the housing is variable from one element to the other. This set of elements enables the surgeon to select the element with the most appropriate geometry once the base has been immobilized on the patient's glenoid cavity.

The invention also relates to a total shoulder prosthesis which comprises a s glenoidal component as mentioned hereinabove or of which the element which forms the convex surface of articulation has been selected from a set of elements as mentioned hereinabove.

Finally, the invention relates to a method for installing a glenoidal component of a shoulder prosthesis, which may be carried out with a component as described hereinabove and, more specifically, to a method comprising steps consisting in:
immobilizing on the patient's glenoid cavity the base of the glenoidal component;
selecting from a plurality of elements adapted to be added on this base and of which the geometric centres of the parts of articular surfaces in the form of portion of sphere are offset differently with respect to a central axis of a housing for at least partially receiving a part of this base, an element of which the geometric centre of the part of surface in the form of portion of sphere will, once mounted on the base, be in a predetermined position, and mounting the selected element on the base.

BRIEF DESCRIPTION OF THE DRAWINGS

The invention will be more readily understood and other advantages thereof will appear more clearly in the light of the following description of a form of embodiment of a glenoidal component and of a prosthesis in accordance with its principle, given solely by way of example and made with reference to the accompanying drawings, in which.

DESCRIPTION OF PREFERRED EMBODIMENT

Figure 1:
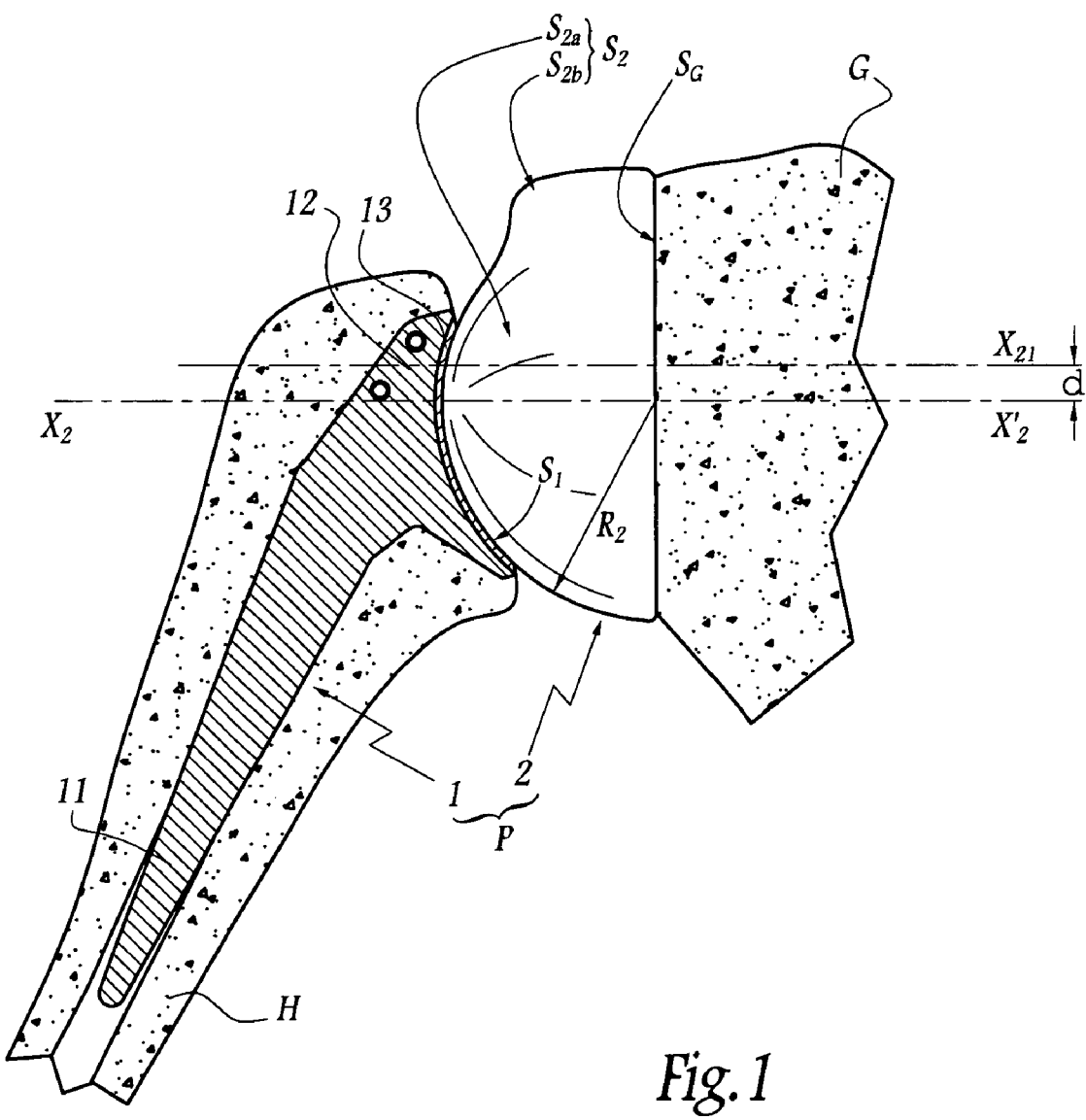
FIG. 1 schematically shows a shoulder prosthesis according to the invention, implanted on a patient.

Referring now to the drawings, the prosthesis P shown in FIG. 1 comprises a humeral component 1 composed of a stem 11 intended to be anchored in the medullary canal of the humerus H, as well as of a metaphyseal part 12 in which is immobilized a cup 13 made of polyethylene defining a concave articular surface $S_1$ in the form of a portion of sphere.

The prosthesis P also comprises a glenoidal component 2 which defines a convex articular surface $S_2$ and which is intended to be implanted on the glenoid cavity G of the shoulder after the latter has been milled in order to create a surface $S_G$ globally parallel to a vertical plane (not shown) containing the spinal column of the patient when he/she is standing up.

In order to render the drawing clearer, the component 1 is shown in section, while the component 2 is shown seen from the outside in FIG. 1.

The surface $S_2$ comprises a portion $S_{2a}$ globally in the form of a demi-sphere, centred on a geometric point $C_2$ and of radius $R_2$.

Figure 2:
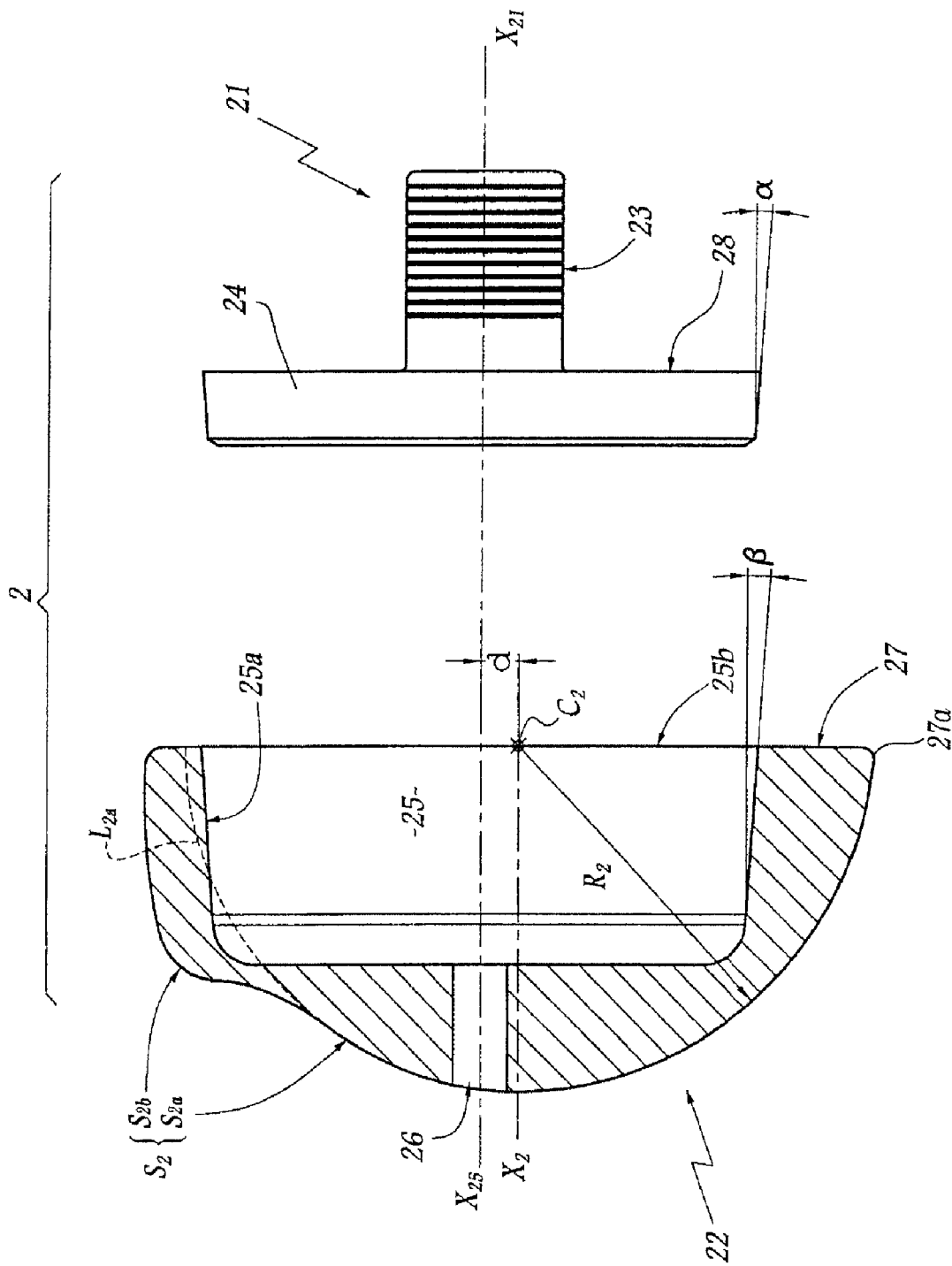
FIG. 2 is an exploded view, partially in section, of a glenoidal component of the prosthesis of FIG. 1.

As is more particularly visible in FIG. 2, the glenoidal component 2 is formed by the assembling of two parts, namely a base 21 and an element 22, sometimes called "head", which defines the surface $S_2$ and which is intended to be mounted on the base 21 when the latter has been anchored on the glenoid cavity G.

The base 21 globally presents symmetry of revolution and $X_{21}$ denotes its central axis. The base 21 comprises a stem 23 for anchoring, intended to be introduced in a corresponding bore to be made in the glenoid cavity G as well as a part 24 intended to project with respect to the surface $S_G$ when the base 21 is implanted. The part 24 is truncated and α denotes its semi-vertex angle.

In FIG. 2, the base 21 is shown from the outside, while the head 22 is represented in section in a plane of symmetry.

The head 22 defines a housing 25 for receiving the part 24 when the head 22 is mounted on the base 21. This housing 25 is centred on an axis of symmetry $X_{25}$ which is merged with the axis $X_{21}$ when the component 2 is in assembled configuration.

The peripheral surface 25a of the housing 25 is globally truncated and divergent in the direction of its mouth 25b, with a semi-vertex angle β of value substantially equal to that of the semi-vertex angle α, this making it possible to obtain an immobilization of the glenoidal head 22 on the base 21 in the manner of a Morse cone.

A bore 26 centred on axis $X_{25}$ makes it possible to access the housing 25 from the outside, i.e. opposite the surface 27 of the head 22 which is normally turned towards the surface $S_G$ milled in the glenoid cavity. This orifice 26 allows the surgeon to manipulate a means for tightening the head 22 on the base 21 such as known, for example, from FR-A-2 835 425.

The centre $C_2$ of the surface $S_2$ is not aligned on the axis $X_{25}$ but offset with respect thereto by a non-zero distance d. $X_2$ denotes an axis perpendicular to the surface 27 and passing through the centre $C_2$. This axis is an axis of symmetry of the spherical part $S_{2a}$ of the surface $S_2$ extended by an imaginary surface of which the trace is represented by the broken arcuate line $L_{2a}$ in FIG. 2. An imaginary hemispherical surface congruent to the part $S_{2a}$ may in effect be considered. The trace of this surface in FIG. 2 would be an arc of circle centred on point $C_2$ and formed by the join of the arc of circle representing the part $S_{2a}$ and by the line $L_{2a}$. The axis $X_2$ would in that case be an axis of symmetry of this surface.

The axis $X_2$ is parallel to axis $X_{25}$ and, when the head 22 is in mounted configuration, to axis $X_{21}$.

The centre $C_2$ defines the position of the part $S_{2a}$ of the surface $S_2$ which is that which effectively interacts with the surface $S_1$ of the humeral component 1.

When the glenoidal component 2 is assembled, the centre $C_2$ is offset with respect to the axis $X_{21}$ by the distance d which is non-zero, this making it possible to lower the active part $S_{2a}$ of the surface $S_2$ for a better positioning of the prosthesis with respect to the patient's scapula.

As the portion $S_{2a}$ of the surface $S_2$ would not allow the head 22 to include the housing 25 taking into account the offset d, an out-of-true transition surface $S_{2b}$ extends the portion $S_{2a}$ up to the edge 27a of the surface 27 in its part most remote from the centre $C_2$. The fact that the surface $S_{22}$ is not hemispherical does not hinder functioning of the prosthesis P insofar as this surface does not normally interact with the surface $S_1$.

On this subject, it may be imagined, within the scope of the present invention, that the head 22 is truncated in its upper part shown in FIG. 2, i.e. that the surface 25a is interrupted in its part which projects from the line $L_{2a}$ in FIG. 2, since this part does not normally interact with the surface $S_1$.

Figure 3:
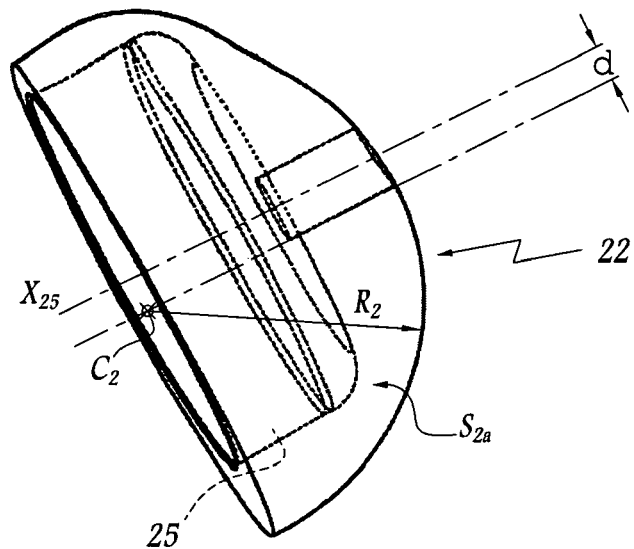
FIG. 3 is a view in perspective of an element constituting the glenoidal component of FIG. 2.
Figure 4:
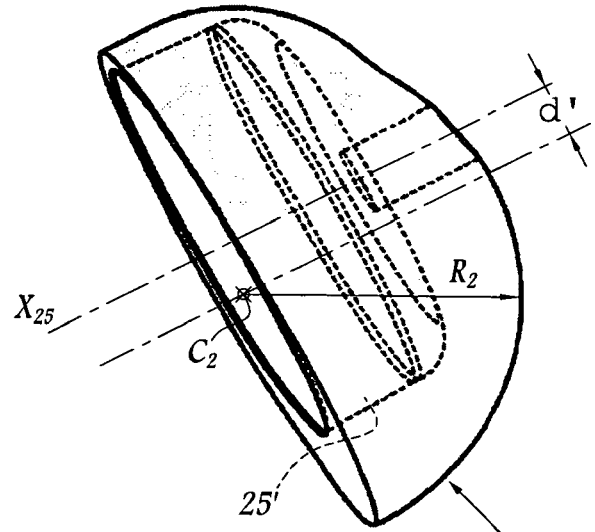
FIG. 4 is a view similar to FIG. 3 for a second element capable of belonging to a glenoidal component as shown in FIG. 2.
Figure 5:
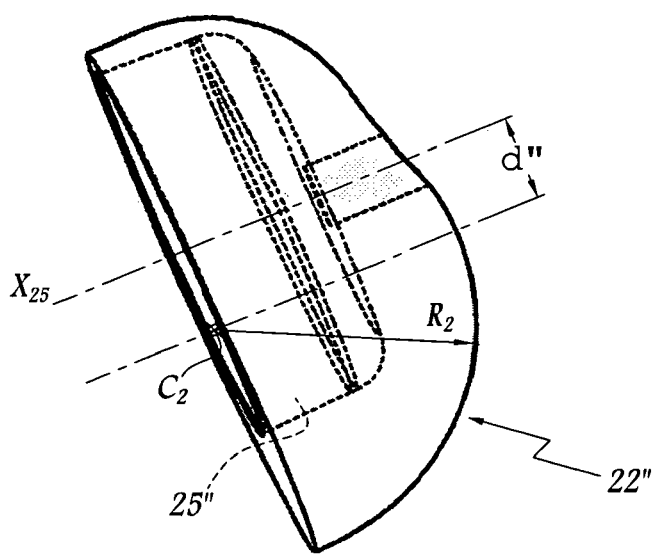
FIG. 5 is a view similar to FIG. 3 for a third element capable of belonging to a glenoidal component as shown in FIG. 2.

As is more particularly apparent on comparing FIGS. 3 to 5, different heads 22, 22' and 22" may be mounted on the base 21, these heads having different offsets d, d' and d" between the geometric centres $C_2$ of the hemispherical portions of the surfaces $S_2$ that they define and the central axes $X_{25}$ of the housings 25, 25', 25" that they likewise define. The offsets d, d', d" correspond, once one of these heads is mounted on a base, to the offsets between the centres $C_2$ and the axis $X_{21}$.

In this way, the three glenoidal heads respectively shown in FIGS. 3 to 5 constitute a set of elements that may be selectively added on a base 21 and of which one may be selected by the surgeon after the base has been anchored on the glenoid cavity so that its centre $C_2$ is in a predetermined position which takes into account the geometry of the glenoid cavity and/or the position of the concave articular surface $S_1$ of the humeral element.

The installation of a prosthesis according to the invention therefore allows the surgeon, after having anchored the base 21 of the glenoidal component, to adjust the position of the convex articular surface $S_2$ by a reasoned choice of the glenoidal head 22, 22', 22", and this in order to improve the patient's comfort.

When this choice has been effected, it suffices for the surgeon to mount the selected head on the base and to immobilize it by any appropriate means.

According to a variant of the invention (not shown), the axis $X_2$ of the hemispherical part $S_{2a}$ of the surface $S_2$ is not necessarily perpendicular to the rear face 28 of the part 24 or to the surface 27 of the head 22 which come into abutment or are parallel to the surface $S_G$. This makes it possible to correct a defect in parallelism between the surface $S_G$ and the aforementioned plane containing the spinal column of the patient in standing position, thanks to a "cant" of the hemispherical part of the surface $S_2$ with respect to the surface $S_G$.

What is claimed is:

1. A glenoidal component for a reverse shoulder prosthesis that is adapted to secure to a surface of a glenoid cavity, the glenoidal component comprising:
   a base adapted to be secured to the surface of the glenoid cavity, the base comprising a mounting portion adapted to receive a single element and a rear surface adapted to engage at least a portion of the surface of the glenoid cavity; and
   a plurality of elements, each comprising a convex articular surface and a recess adapted to engage with the mounting portion of the base, the convex articular surface comprising a non-spherical portion and a spherical portion with a geometric center and an axis of symmetry that passes through the geometric center, wherein in an engaged configuration an offset between the geometric center of the spherical portion and an axis of symmetry of the recess varies between at least two of the elements.

2. The glenoidal component of claim 1 wherein the base comprises a stem adapted to secure to the glenoid cavity.

3. The glenoidal component of claim 1 wherein the mounting portion comprises a truncated cone.

4. The glenoidal component of claim 1 wherein the mounting portion of the base comprises a central axis that is collinear with the axis of symmetry of the recess on at least one of the elements.

5. The glenoidal component of claim 1 wherein the mounting portion of the base comprises a central axis that is parallel with the axis of symmetry of the recess on at least one of the elements.

6. The glenoidal component of claim 1 wherein the mounting portion of the base comprises a central axis that is parallel with the axis of symmetry of the spherical portion on at least one of the elements.

7. The glenoidal component of claim 1 wherein the axis of symmetry of the spherical portion of at least one element is not perpendicular to a rear face of the element.

8. The glenoidal component of claim 1 wherein the mounting portion of the base extends only partially into the recess on at least one of the elements.

9. The glenoidal component of claim 1 wherein the base comprises a center axis that is generally perpendicular to the rear surface.

10. The glenoidal component of claim 1 wherein the axis of symmetry of the spherical portion is parallel to the axis of symmetry of the recess on at least one of the elements.

11. The glenoidal component of claim 1 wherein the axis of symmetry of the spherical portion is perpendicular to a rear surface of the element on at least one of the elements.

12. The glenoidal component of claim 1 wherein the axis of symmetry of the spherical portion on at least one of the elements is perpendicular to the rear surface of the base in the engaged configuration.

13. The glenoidal component of claim 1 comprising at least one element with a geometric center of the spherical portion located on the axis of symmetry of the recess.

14. The glenoidal component of claim 1 wherein each of the elements comprises a different offset.

15. The glenoid component of claim 1 wherein the plurality of elements comprise:
    a first element with an axis of symmetry of the spherical portion offset from the axis of symmetry of the recess by a first distance; and
    a second element with an axis of symmetry of the spherical portion offset from the axis of symmetry of the recess by a second distance different from the first distance.

16. Glenoidal component of a reverse shoulder prosthesis adapted to secure to a surface of a glenoid cavity, the glenoidal component comprising:
    a base comprising a rear surface adapted to engage with at least a portion of the surface of the glenoid cavity, and a mounting portion with a center axis adapted to receive a single element; and
    a plurality of elements, each comprising a convex articular surface including a non-spherical portion, a spherical portion with a geometric center, and a recess adapted to engage with the mounting portion of the base so that an offset between the geometric center and the center axis of the base varies between at least two elements.

17. A reverse shoulder prosthesis with a system of glenoidal components adapted to secure to a surface of a glenoid cavity, the system comprising:
    a humeral stem with a concave articular surface;
    a base adapted to be secured to the surface of the glenoid cavity, the base comprising a mounting portion and a rear surface adapted to engage at least a portion of the surface of the glenoid cavity; and
    a plurality of elements each comprising a convex articular surface adapted to engage with the concave articular surface on the humeral stem and a recess adapted to engage with the mounting portion of the base, the convex articular surface comprising a non-spherical portion and a spherical portion with a geometric center and an axis of symmetry that passes through the geometric center, wherein in an engaged configuration an offset between the geometric center and an axis of symmetry of the recess varies between at least two elements.

18. A method of implanting a glenoidal component for a reverse shoulder prosthesis to a surface of a glenoid cavity, the method comprising the steps of:
    engaging a rear surface of a base with at least a portion of the prepared surface of the glenoid cavity;
    securing the base to the prepared surface of the glenoid cavity;
    selecting a first element from a plurality of elements comprising a convex articular surface having a non-spherical portion and a spherical portion, and a recess adapted to engage with a mounting portion on the base;
    engaging the recess on the first element with the mounting portion on the base so that a geometric center of the spherical portion on the convex articular surface is offset from an axis of symmetry of the recess by a first distance;

removing the first element from the mounting portion;

selecting a second element from the plurality of elements, the second element comprising a convex articular surface having a non-spherical portion and a spherical portion, and a recess adapted to engage with the mounting portion on the base;

engaging the recess on the second element with the mounting portion on the base so that a geometric center of the spherical portion on the convex articular surface on the second element is offset from an axis of symmetry of the recess by a second distance different from the first distance; and selecting one of the first or second elements.

\* \* \* \* \*

UNITED STATES PATENT AND TRADEMARK OFFICE
CERTIFICATE OF CORRECTION

PATENT NO.        : 7,462,197 B2
APPLICATION NO.   : 11/151404
DATED             : December 9, 2008
INVENTOR(S)       : Alain Tornier et al.

Page 1 of 1

It is certified that error appears in the above-identified patent and that said Letters Patent is hereby corrected as shown below:

On Page 1 of the Title Page:
Item (75) Inventors:
After Gilles Walch: remove "Lyons" and replace it with -- Lyon --

On Page 3 of the Title Page: item (56);
Under U.S. Patent Documents:
Remove "2002/0136148 A1" and replace it with -- 2002/0138148 A1 --
Remove "2005/0276030 A1  12/2005 Tornier et al."

Under Foreign Patent Documents:
Remove "WO 98/48172" and replace it with -- WO 98/46172 --

Signed and Sealed this

Fourteenth Day of April, 2009

JOHN DOLL
*Acting Director of the United States Patent and Trademark Office*